US011472729B2

(12) United States Patent
Yamada et al.

(10) Patent No.: US 11,472,729 B2
(45) Date of Patent: Oct. 18, 2022

(54) SILICATE GLASS AND DENTAL PRODUCT

(71) Applicant: KURARAY NORITAKE DENTAL INC., Kurashiki (JP)

(72) Inventors: Kazuhiro Yamada, Aichi (JP); Toshio Sakakibara, Aichi (JP); Kiyoko Ban, Aichi (JP)

(73) Assignee: KURARAY NORITAKE DENTAL INC., Kurashiki (JP)

(*) Notice: Subject to any disclaimer, the term of this patent is extended or adjusted under 35 U.S.C. 154(b) by 0 days.

(21) Appl. No.: 16/761,635

(22) PCT Filed: Nov. 6, 2018

(86) PCT No.: PCT/JP2018/041211
§ 371 (c)(1),
(2) Date: May 5, 2020

(87) PCT Pub. No.: WO2019/093336
PCT Pub. Date: May 16, 2019

(65) Prior Publication Data
US 2021/0179481 A1 Jun. 17, 2021

(30) Foreign Application Priority Data

Nov. 7, 2017 (JP) ............................. JP2017-214498

(51) Int. Cl.
*C03C 3/087* (2006.01)
*A61K 6/833* (2020.01)
*C03C 10/00* (2006.01)

(52) U.S. Cl.
CPC .............. *C03C 3/087* (2013.01); *A61K 6/833* (2020.01); *C03C 10/0036* (2013.01)

(58) Field of Classification Search
CPC ....... C03C 3/087; C03C 10/0036; A61K 6/833
See application file for complete search history.

(56) References Cited

U.S. PATENT DOCUMENTS

| 4,455,383 A | 6/1984 | Panzera |
| 5,775,912 A | 7/1998 | Panzera et al. |
| 5,849,068 A * | 12/1998 | Hofmann, geb. Roth ............... A61C 13/04 106/35 |
| 6,342,302 B1 | 1/2002 | Steidl et al. |
| 2003/0129329 A1* | 7/2003 | Grossman ............... C23C 30/00 428/34.1 |
| 2004/0121894 A1* | 6/2004 | Brodkin .................. C03C 3/087 501/16 |
| 2020/0405586 A1 | 12/2020 | Hauptmann et al. |
| 2021/0002181 A1 | 1/2021 | Rothbrust et al. |

FOREIGN PATENT DOCUMENTS

| JP | 5-194130 A | 8/1993 |
| JP | 10-75964 A | 3/1998 |
| JP | 2007-308415 A | 11/2007 |
| JP | 2016-216300 A | 12/2016 |
| JP | 2017-122064 A | 7/2017 |
| WO | WO 00/48956 A1 | 8/2000 |

OTHER PUBLICATIONS

Extended European Search Report dated Aug. 2, 2021 in European Patent Application No. 18876865.9, citing documents AA, AB and AO therein, 6 pages.
Ozawa, M. et al., "An Analysis of Fused Interface between Veneering Porcelain and Zirconia," Annals of Japan Prosthodontic Society, vol. 3., No. 4, 2011, pp. 336-345.
International Search Report dated Feb. 5, 2019 in PCT/JP2018/041211 filed on Nov. 6, 2018, citing documents AA, AO-AR and AW therein, 2 pages.

* cited by examiner

*Primary Examiner* — Karl E Group
*Assistant Examiner* — Cameron K Miller
(74) *Attorney, Agent, or Firm* — Oblon, McClelland, Maier & Neustadt, L.L.P.

(57) ABSTRACT

The present invention provides a silicate glass that can reduce a color change in base material zirconia even when simultaneously fired with an unsintered zirconia. The present invention also provides a dental product using same. The present invention relates to a silicate glass comprising: 65.0 to 90.0 mol % $SiO_2$, 4.0 to 15.0 mol % $Al_2O_3$, 1.0 to 10.0 mol % $K_2O$, 0.1 to 7.0 mol % $Na_2O$, and 0.01 to 15.0 mol % CaO, the silicate glass being essentially free of $B_2O_3$, and satisfying the relation {(number of moles of $Al_2O_3$)/(total number of moles of $RO+R_2O$)}≥0.70, wherein R in the metal oxide represented by RO represents a metallic element in group 2 or 12 of the periodic table, and R in the metal oxide represented by $R_2O$ represents a metallic element in group 1 of the periodic table. The present invention also relates to a composite comprising the silicate glass and a base material formed of a ceramic; a sintered body as a fired product of the composite; and a dental product comprising the sintered body.

11 Claims, No Drawings

SILICATE GLASS AND DENTAL PRODUCT

TECHNICAL FIELD

The present invention relates to a silicate glass, and a dental product having a silicate glass.

BACKGROUND ART

For years, metal has been used for a range of dental products (for example, prostheses such as veneer crowns, dental caps, crowns, and post crowns). However, metals lack aesthetic quality, and can cause allergic reaction when released from these products. These issues involving the use of metal have been addressed by dental products that replace metals with ceramic materials such as alumina (aluminum oxide) and zirconia (zirconium oxide). Zirconia, in particular, has desirable aesthetic quality and strength, and this, combined with the current declining prices of zirconia, has created a high demand for this material.

For improved oral aesthetics, a dental product must match the appearance of natural teeth. It is, however, difficult to reproduce the appearance of natural teeth (particularly, transparency, gloss (luster), and color) with zirconia (sintered body) alone. This is overcome by fusing silicate glass, called porcelain, into an exposed surface of a zirconia frame, instead of leaving the zirconia surface exposed, to provide a veneer crown made to reproduce the appearance of natural teeth. Such dental products are produced by firing zirconia, and fusing silicate glass as a dental porcelain. Dental products produced in this fashion are called porcelain fused to zirconia (PFZ) crowns.

As a rule, a zirconia sintered body does not have the transparency and gloss of natural teeth. In order to reproduce the appearance of natural teeth, it is accordingly desired that the dental-porcelain side of PFZ have the color and gloss of natural teeth with the dental porcelain fused to the frame made of a zirconia sintered body. For example, Patent Literature 1 proposes such a dental porcelain by disclosing a coating material for dental prostheses.

CITATION LIST

Patent Literature

Patent Literature 1: JP H05-194130 A

SUMMARY OF INVENTION

Technical Problem

There exists a need for one day treatment, a medical service that offers intraoral placement of a dental product in one visit (in one day). Seeing the growing demands for process simplicity and shorter fabrication times, the present inventors have conducted studies to achieve a simpler process and a shorter fabrication time for a method of producing a dental product containing a base material formed of a sintered body, specifically by applying or layering a dental porcelain on a base material formed of an unsintered body, and firing the base material and the dental porcelain at the same time.

The invention disclosed in Patent Literature 1 is a coating material for dental prostheses, and the coating material is described as being coated on a dental prosthesis made of zirconia material. It is reported in this related art document that the coating material for dental prostheses is coated and fused to a surface of a sintered body such as zirconium metal. The coating material for dental prostheses comprises a glass containing, in weight %, 62 to 75% $SiO_2$, 3 to 15% $Al_2O_3$, 4 to 10% $Li_2O$, 4 to 15% $Na_2O$, and 5.5 to 15% $ZrO_2$ and/or $HfO_2$ as its constituent components.

However, the coating material for dental prostheses described in Patent Literature 1 is firable at a temperature of at most 950° C. because of the distribution of its constituent components in the composition, and, when applied to an unsintered zirconia and fired at the same time using the method being investigated by the present inventors to achieve a simpler process and a shorter fabrication time, the coating material would probably produce a PFZ that does not have the color and gloss of natural teeth as a result of discoloration (color difference) occurring in the zirconia sintered body forming the base material.

It is accordingly an object of the present invention to provide a silicate glass that can reduce a color change in base material zirconia even when simultaneously fired with an unsintered zirconia. Another object of the present invention is to provide a composite comprising the silicate glass and a base material, a sintered body thereof, and a dental product thereof.

Solution to Problem

The present inventors conducted intensive studies to find a solution to the foregoing problem, and found that a zirconia sintered body after firing of a silicate glass applied thereon, and a zirconia sintered body after simultaneous firing of an unsintered zirconia and a silicate glass can have a smaller color difference when the contents of the constituent components $SiO_2$, $Al_2O_3$, $K_2O$, $Na_2O$, and CaO of the silicate glass are confined within predetermined ranges. The present invention was completed after further studies conducted on the basis of this finding.

Specifically, the present invention relates to the following.

[1] A silicate glass comprising:
  65.0 to 90.0 mol % $SiO_2$,
  4.0 to 15.0 mol % $Al_2O_3$,
  1.0 to 10.0 mol % $K_2O$,
  0.1 to 7.0 mol % $Na_2O$, and
  0.01 to 15.0 mol % CaO,
the silicate glass being essentially free of $B_2O_3$, and satisfying the relation {(number of moles of $Al_2O_3$)/(total number of moles of $RO+R_2O$)}≥0.70, wherein R in the metal oxide represented by RO represents a metallic element in group 2 or 12 of the periodic table, and R in the metal oxide represented by $R_2O$ represents a metallic element in group 1 of the periodic table.

[2] The silicate glass of [1], comprising:
  69.0 to 89.0 mol % $SiO_2$,
  5.0 to 13.0 mol % $Al_2O_3$,
  3.0 to 9.0 mol %
  1.0 to 4.0 mol % $Na_2O$, and
  0.05 to 13.0 mol % CaO,
the silicate glass being essentially free of $B_2O_3$, and satisfying the relation {(number of moles of $Al_2O_3$)/(total number of moles of $RO+R_2O$)}≥0.70.

[3] The silicate glass of [1] or [2], wherein the silicate glass is essentially free of ZnO.

[4] The silicate glass of any one of [1] to [3], wherein the silicate glass is essentially free of MgO, BaO, and SrO.

[5] The silicate glass of any one of [1] to [4], wherein the silicate glass has a suitable firing temperature of 1,100° C. or more.

[6] The silicate glass of any one of [1] to [5], wherein the silicate glass has a coefficient of thermal expansion of $11.0 \times 10^{-6} K^{-1}$ or less as measured in compliance with ISO 6872:2015.
[7] The silicate glass of any one of [1] to [6], wherein the silicate glass further comprises at least one selected from the group consisting of a pigment and an opacifying agent.
[8] A composite comprising the silicate glass of any one of [1] to [7], and a ceramic.
[9] The composite of [8], wherein the ceramic is a zirconia ceramic.
[10] A sintered body of the composite of [8] or [9].
[11] A dental product comprising the sintered body of [10].

Advantageous Effects of Invention

With a silicate glass of the present invention, a color change that occurs in a zirconia sintered body forming a base material can be reduced even when the silicate glass is simultaneously fired with an unsintered zirconia at a firing temperature of the zirconia. That is, the present invention has enabled an unsintered zirconia and a silicate glass to be simultaneously used for firing, making it possible to conveniently and quickly obtain a dental product containing a sintered body.

DESCRIPTION OF EMBODIMENTS

A silicate glass of the present invention comprises 65.0 to 90.0 mol % $SiO_2$, 4.0 to 15.0 mol % $Al_2O_3$, 1.0 to 10.0 mol % $K_2O$, 0.1 to 7.0 mol % $Na_2O$, and 0.01 to 15.0 mol % CaO, and is essentially free of $B_2O_3$.

In this specification, the notation (for example, "$SiO_2$") used for the constituent components of the silicate glass assumes that the elements (for example, a metal such as Si) contained in the silicate glass exist as oxides. Specifically, for example, a metallic element will be denoted as forming an oxide even if it is forming a composite with another metallic element. Likewise, the content of each component contained in the silicate glass means the oxide content of the element assumed as forming an oxide.

The silicate glass of the present invention comprises $SiO_2$ as a constituent component. The $SiO_2$ content is 65.0 mol % or more, preferably 69.0 mol % or more, more preferably 69.8 mol % or more relative to the total number of moles of the constituent components of the silicate glass. A $SiO_2$ content of less than 65.0 mol % results in a silicate glass having an excessively low suitable firing temperature. The $SiO_2$ content is 90.0 mol % or less, preferably 89.0 mol % or less, more preferably 88.7 mol % or less relative to the total number of moles of the constituent components of the silicate glass. A $SiO_2$ content of more than 90.0 mol % results in an excessively high suitable firing temperature.

The silicate glass of the present invention comprises $Al_2O_3$ as a constituent component. The $Al_2O_3$ content is 4.0 mol % or more, preferably 5.0 mol % or more, more preferably 5.7 mol % or more relative to the total number of moles of the constituent components of the silicate glass. An $Al_2O_3$ content of less than 4.0 mol % results in an excessively low suitable firing temperature. The $Al_2O_3$ content is 15.0 mol % or less, preferably 13.0 mol % or less, more preferably 12.7 mol % or less relative to the total number of moles of the constituent components of the silicate glass. An $Al_2O_3$ content of more than 15.0 mol % results in an excessively high suitable firing temperature.

In view of suitable firing temperature, the $Al_2O_3$ content needs to be 0.70 or more, and is preferably 0.72 or more, more preferably 0.85 or more in terms of a mole ratio of the silicate glass composition, specifically, a mole ratio of $Al_2O_3$ relative to the total amount of basic components ($RO+R_2O$) in moles: {(number of moles of $Al_2O_3$)/(total number of moles of $RO+R_2O$)}. As used herein, "basic component" refers to a metal oxide constituting the silicate glass of the present invention and represented by general formula RO or $R_2O$. R in the metal oxide represented by RO represents a metallic element in group 2 or 12 of the periodic table. Examples of RO include ZnO, CaO, MgO, BaO, and SrO. R in the alkali metal oxide represented by $R_2O$ represents a metallic element in group 1 of the periodic table. Examples of $R_2O$ include $Li_2O$, $Na_2O$, and $K_2O$. The upper limit of the mole ratio {(number of moles of $Al_2O_3$)/(total number of moles of $RO+R_2O$)} concerning the contents of $Al_2O_3$ and basic components ($RO+R_2O$) is not particularly limited, and may be 3.0 or less, 2.0 or less, 1.5 or less, or 1.3 or less. Another embodiment of the silicate glass of the present invention is a silicate glass in which {(number of moles of $Al_2O_3$)/(total number of moles of $CaO+Al_2O_3+K_2O+Na_2O$)} is 0.70 or more, when the metal oxide represented by RO is consisting essentially of CaO.

In certain embodiments of the silicate glass of the present invention, the content (number of moles) of $R_2O$ is preferably greater than the content (number of moles) of RO because it enhances the effect of reducing a color change of the base material zirconia even when the silicate glass is simultaneously fired with an unsintered zirconia. Specifically, it is preferable that the silicate glass of the present invention satisfy 1.0<{(number of moles of $R_2O$)/(number of moles of RO)}<300, more preferably 1.2<{(number of moles of $R_2O$)/(number of moles of RO)}<200, even more preferably 1.4<{(number of moles of $R_2O$)/(number of moles of RO)}<150.

The silicate glass of the present invention comprises $K_2O$ as a constituent component. The $K_2O$ content is 1.0 mol % or more, preferably 3.0 mol % or more, more preferably 3.6 mol % or more relative to the total number of moles of the constituent components of the silicate glass. A $K_2O$ content of less than 1.0 mol % may result in unstable vitrification. The $K_2O$ content is 10.0 mol % or less, preferably 9.0 mol % or less, more preferably 8.3 mol % or less relative to the total number of moles of the constituent components of the silicate glass. A $K_2O$ content of more than 10.0 mol % increases the coefficient of thermal expansion.

The silicate glass of the present invention comprises $Na_2O$ as a constituent component. The $Na_2O$ content is 0.1 mol % or more, preferably 1.0 mol % or more, more preferably 1.7 mol % or more relative to the total number of moles of the constituent components of the silicate glass. A $Na_2O$ content of less than 0.1 mol % may result in unstable vitrification. The $Na_2O$ content is 7.0 mol % or less, preferably 4.0 mol % or less, more preferably 3.8 mol % or less relative to the total number of moles of the constituent components of the silicate glass. A $Na_2O$ content of more than 7.0 mol % increases the coefficient of thermal expansion.

The silicate glass of the present invention comprises CaO as a constituent component. The CaO content is 0.01 mol % or more, preferably 0.05 mol % or more, more preferably 0.1 mol % or more relative to the total number of moles of the constituent components of the silicate glass. With a CaO content of 0.01 mol % or more, CaO is able to act as a flux in the glass. The CaO content is 15.0 mol % or less, preferably 13.0 mol % or less, more preferably 12.2 mol % or less relative to the total number of moles of the constituent components of the silicate glass. In this way, a silicate glass can be obtained that has a desirable suitable firing temperature and a desirable coefficient of thermal expansion.

In the silicate glass of the present invention, the content (number of moles) of $K_2O$ is preferably greater than the content (number of moles) of $Na_2O$ because it enhances the effect of reducing a color change of the base material zirconia even when the silicate glass is simultaneously fired with an unsintered zirconia. Specifically, it is preferable that the silicate glass of the present invention satisfy 1.0<{(number of moles of $K_2O$)/(number of moles of $Na_2O$)}, more preferably 1.5<{(number of moles of $K_2O$)/(number of moles of $Na_2O$)}, even more preferably 2.0<{(number of moles of $K_2O$)/(number of moles of $Na_2O$)}. The upper limit value of {(number of moles of $K_2O$)/(number of moles of $Na_2O$)} as a mole ratio of $K_2O$ and $Na_2O$ is not particularly limited, and may be less than 100, less than 50, or less than 30.

For purposes such as adjustments of the properties of the silicate glass or a sintered body obtained therefrom (e.g., adjustments of color, fluorescence, and transmittance), the silicate glass of the present invention may further comprise at least one selected from the group consisting of a pigment and an opacifying agent (opacifier). At least one selected from the group consisting of a pigment and an opacifying agent (opacifier) may or may not be a constituent component of the silicate glass of the present invention. The pigment may be, for example, an oxide of at least one element selected from the group consisting of P, Ti, V, Cr, Mn, Fe, Co, Ni, Zn, Y, Zr, Sn, Sb, Bi, Ce, Pr, Sm, Eu, Gd, Tb, and Er. Examples of such oxides include $CoO$, $NiO$, $Fe_2O_3$, and $Cr_2O_3$. The pigment may be a fluorescent pigment. The opacifying agent may be, for example, at least one compound selected from the group consisting of $TiO_2$, $ZrO_2$, $ZrSiO_4$, $SnO_2$, and $CeO_2$. Individually, the pigment and the opacifying agent contained in the silicate glass may be one kind of compound, or two or more kinds of compounds. The individual contents of the pigment and the opacifying agent may be 0.001 to 3.0 mol %, 0.01 to 1.0 mol %, or 0.01 to 0.1 mol % relative to the total number of moles of the constituent components of the silicate glass.

The silicate glass of the present invention is essentially free of $B_2O_3$ because $B_2O_3$, when contained in the silicate glass, lowers the suitable firing temperature. In certain embodiments, the silicate glass of the present invention may be essentially free of $HfO_2$. In other embodiments, the silicate glass of the present invention may comprise $Li_2O$, or may be essentially free of $Li_2O$. When the silicate glass is containing $Li_2O$, the $Li_2O$ content may be 0.1 to 5.0 mol %, or 0.1 to 1.0 mol % relative to the total number of moles of the constituent components of the silicate glass. In yet other embodiments, the silicate glass of the present invention may comprise MgO, or may be essentially free of MgO. When the silicate glass is containing MgO, the MgO content may be 0.1 to 9.0 mol %, 0.3 to 8.0 mol %, or 0.5 to 6.0 mol % relative to the total number of moles of the constituent components of the silicate glass. In other embodiments, the silicate glass of the present invention may comprise BaO, or may be essentially free of BaO. When the silicate glass is containing BaO, the BaO content may be 0.1 to 5.0 mol %, 0.3 to 4.0 mol %, or 0.5 to 2.0 mol % relative to the total number of moles of the constituent components of the silicate glass. In certain embodiments, the silicate glass of the present invention may comprise SrO, or may be essentially free of SrO. When the silicate glass is containing SrO, the SrO content may be 0.1 to 5.0 mol %, 0.3 to 4.0 mol %, or 0.5 to 2.0 mol % relative to the total number of moles of the constituent components of the silicate glass. In certain embodiments, the silicate glass of the present invention may comprise ZnO, or may be essentially free of ZnO. When the silicate glass is containing ZnO, the ZnO content may be 0.1 to 5.0 mol %, 0.3 to 4.0 mol %, or 0.5 to 2.0 mol % relative to the total number of moles of the constituent components of the silicate glass. As used herein, "essentially free" of a component means that the content of the component is less than 0.1 mol %, preferably less than 0.05 mol %, more preferably less than 0.01 mol % relative to the total number of moles of the constituent components of the silicate glass.

The silicate glass of the present invention may have, for example, a form of a powder. The powder has an average particle diameter (d50) of preferably 75 μm or less, more preferably 50 μm or less, even more preferably 40 μm or less. The average particle diameter (d50) of powder may be measured using a laser diffraction particle size distribution analyzer (MT3300EXII, manufactured by MicrotracBEL Corp.).

The silicate glass of the present invention has a suitable firing temperature of preferably 1,100° C. or more, more preferably 1,200° C. or more, even more preferably 1,350° C. or more. With the suitable firing temperature falling in these ranges, it is possible to reduce discoloration of the base material, for example, when the silicate glass is used as a dental porcelain, and simultaneously fired with the base material. In the present invention, the suitable firing temperature of the silicate glass can be described as the lowest temperature that produces a smooth surface, and provides a transparency clear enough to show the background in the silicate glass heated in the form of a compact, in other words, the lowest temperature at which the silicate glass can be regarded as being sufficiently fired. For example, heating a powdery silicate glass in the form of a compact typically causes the powders to bind to one another in early stages of heating, and, upon reaching a certain temperature after continuous heating, the compact turns into a state where the surfaces are clear enough to show the background. This temperature can be regarded as the suitable firing temperature. Many times, the compact melts when heated further, and deformation, such as coalescence, due to surface tension starts to occur as a result of the compact being no longer able to maintain its shape. The suitable firing temperature can be determined by the method described in detail in the EXAMPLES section below. The upper limit of suitable firing temperature is not particularly limited. The suitable firing temperature may be 1,800° C. or less.

The silicate glass of the present invention has a coefficient of thermal expansion of preferably $11.0 \times 10^{-6} K^{-1}$ or less, more preferably $10.5 \times 10^{-6} K^{-1}$ or less, even more preferably $10.0 \times 10^{-6} K^{-1}$ or less, particularly preferably $9.9 \times 10^{-6} K^{-1}$ or less. With the coefficient of thermal expansion falling in these ranges, it is possible to more effectively reduce defects such as deformation and cracking when the silicate glass of the present invention is heated as a dental porcelain after being applied to the base material. The coefficient of thermal expansion can be measured using the method described in detail in the EXAMPLES section below.

The crystal system of the silicate glass of the present invention is not particularly limited, and may be cristobalite or amorphous. The crystal system can be measured by confirming the X-ray diffraction (XRD) pattern, as will be described in the EXAMPLES section below.

With the silicate glass of the present invention, a color change that occurs in the zirconia sintered body forming the base material can be reduced even when the silicate glass is simultaneously fired with an unsintered zirconia, or simultaneously fired with an unsintered zirconia at a firing temperature of the zirconia. The silicate glass of the present invention has a color difference ΔEa*b*(an index of color change) of preferably 2.7 or less, more preferably 2.0 or less, even more preferably 1.6 or less. The color difference ΔEa*b* can be measured in the manner described in the EXAMPLES section below.

The following describes an example of a method for producing a silicate glass of the present invention.

The method begins with preparation of raw materials, such as oxides, corresponding to the constituent components of a silicate glass to be produced. After drying, the raw materials are weighed according to the composition, and mixed to prepare a mixture. The mixture is melted at high temperature, and the melt is cooled into a cullet. The temperature applied for melting is not particularly limited, and may be 1,300° C. or more, or 1,400° C. or more. The cullet is then pulverized into a predetermined particle diameter range, and, after optional sieving, a powdery silicate glass is obtained.

The silicate glass obtained in the manner described above may be used directly as, for example, a dental porcelain (described later). Alternatively, for purposes such as adjustments of the properties of the silicate glass or a sintered body obtained therefrom (e.g., adjustments of color, fluorescence, and transmittance), at least one of a pigment and an opacifying agent may be mixed into the silicate glass as desired, as described above, and the resulting mixture, after optional sieving into a predetermined particle diameter range, may be used as a silicate glass containing at least one component selected from the group consisting of a pigment and an opacifying agent.

The silicate glass of the present invention can be used for dental applications, preferably as a dental porcelain. The dental porcelain may be one consisting essentially of the silicate glass. In a dental porcelain consisting essentially of the silicate glass, the content of components other than the silicate glass contained in the dental porcelain is preferably less than 10 mass %, more preferably less than 5 mass %, even more preferably less than 1 mass %.

Another embodiment of the present invention is a composite comprising the silicate glass and a base material, and in which the base material is a ceramic. Another embodiment is a sintered body as a fired product of the composite. Another embodiment is a dental product comprising the sintered body. The material of the base material is not particularly limited, as long as it is a ceramic that is usable in dental applications. However, for advantages such as more notable enhancement of the effects of the present invention, the base material is made of preferably a zirconia ceramic (a ceramic containing $ZrO_2$ as the main component (predominant component)). When using a silicate glass of the present invention as a dental porcelain, it is preferable that the sintered body of the silicate glass of the present invention have a coefficient of thermal expansion close to the coefficient of thermal expansion of the base material. For example, when using a silicate glass of the present invention as a dental porcelain, it is preferable that the material of the base material (e.g., a zirconia ceramic), and the silicate glass used as a dental porcelain have a coefficient of thermal expansion difference of $5.0 \times 10^{-6} K^{-1}$ or less.

Another embodiment of the present invention is a method of use of the silicate glass, comprising the step of applying or layering a dental porcelain formed of a silicate glass of the present invention on a base material made of a ceramic. In the method, the base material is preferably a zirconia ceramic.

Another embodiment of the present invention is a method for producing a sintered body formed of a composite of a silicate glass of the present invention and a ceramic base material. As an example, the method comprises the steps of applying or layering a dental porcelain formed of the silicate glass on the base material, and simultaneously firing the base material and the dental porcelain. In the method, the base material is preferably a core made of a zirconia ceramic. A silicate glass of the present invention is also usable for a method of production comprising the step of applying or layering a dental porcelain formed of a silicate glass of the present invention on a fired ceramic base material, and firing the dental porcelain.

The present invention encompasses combinations of the foregoing features, provided that such combinations made in various forms within the technical idea of the present invention can produce the effects of the present invention. In the present specification, the upper limits and lower limits of numeric ranges (ranges of, for example, contents of components, values calculated from components, and values of physical properties) can be combined appropriately.

EXAMPLES

The following describes the present invention in greater detail by way of Examples. It should be noted that the present invention is in no way limited by the following Examples, and various changes may be made by a person with ordinary skill in the art within the technical idea of the present invention.

Examples 1 to 4 and Comparative Examples 1 and 2

A silicate glass, and a sintered body as a fired product of the silicate glass were fabricated, and measured for various properties using the methods described below. First, the oxides shown in Table 1 were heated at 120° C., and dried to prepare components that constitute the silicate glass. The oxides were weighed so that the silicate glass formed from these constituent components had the composition shown in Table 1. The oxides were mixed using a ball mill.

TABLE 1

|  | $SiO_2$ *1 | $Al_2O_3$ *1 | $K_2O$ *1 | $Na_2O$ *1 | $CaO$ *1 | $Al_2O_3/(RO + R_2O)$ *2 |
| --- | --- | --- | --- | --- | --- | --- |
| Example 1 | 88.7 | 5.7 | 3.8 | 1.7 | 0.1 | 1.018 |
| Example 2 | 75.2 | 12.6 | 8.3 | 3.8 | 0.1 | 1.033 |
| Example 3 | 72.6 | 12.6 | 6.0 | 2.7 | 6.1 | 0.851 |
| Example 4 | 69.8 | 12.7 | 3.6 | 1.7 | 12.2 | 0.726 |
| Com. Ex. 1 | 64.7 | 11.2 | 7.1 | 16.9 | 0.1 | 0.465 |
| Com. Ex. 2 | 84.6 | 3.8 | 4.2 | 6.2 | 1.2 | 0.328 |

*1 Content of each constituent component (mol %)
*2 Mole ratio of $Al_2O_3$ relative to total number of moles of basic components (RO + $R_2O$)

The mixture was charged into a melting crucible, and melted at 1,500° C. in the atmosphere. After being cooled, the melt was formed into a cullet, and pulverized using a ball mill. The pulverized particles were sieved through a #200 mesh sieve, and the resulting powdery silicate glass was used for the various measurements below. The opening of the sieve is in compliance with the nominal opening W of JIS Z 8801-1-2006.

Examples 5 and 6

The oxides shown in Table 1 were heated at 120° C., and dried to prepare components that constitute the silicate glass. The oxides were weighed so that the silicate glass formed from these constituent components had the composition of Example 1 in Example 5, and the composition of Example 4 in Example 6. The oxides were mixed using a ball mill.

The mixture was charged into a melting crucible, and melted at 1,500° C. in the atmosphere. After being cooled, the melt was formed into a cullet, and pulverized using a ball mill. The pulverized particles were sieved through a #200 mesh sieve to prepare a powdery silicate glass. The silicate glass was used for the various measurements below after adding 3.0 mol % NiO as a pigment in Example 5, and 0.01 mol % $TiO_2$ as an opacifying agent in Example 6, relative to 100 mol % silicate glass. The opening of the sieve is in compliance with the nominal opening W of JIS Z 8801-1-2006.

Method of Determination of Suitable Firing Temperature

The powdery silicate glass obtained by using the foregoing method was mixed with purified water to prepare a slurry. The slurry was charged into a cylindrical mold measuring 16 mm in diameter×1.6 mm, and molded into a silicate glass compact after repeated condensation (moisture removal) and moisture absorption. At room temperature, the compact was placed in a furnace (a dental laboratory porcelain furnace (Noritake KATANA™ F-1, manufactured by SK medical electronics Co., Ltd.), and was fired by being heated to an arbitrarily selected specific temperature. Immediately after firing, the compact was allowed to cool to room temperature, and visually inspected for its state produced by firing. Specifically, the compact (sintered body) was checked to see if it had a smooth surface with a transparency clear enough to show the background (i.e., if the compact was properly fired), and was maintaining the original shape before firing (i.e., no deformation due to overfiring). The lowest temperature that produced such a sintered body was determined as the suitable firing temperature of the silicate glass of the present invention. The evaluation results for Examples and Comparative Examples are presented in Table 2.

Method of Confirmation of Crystal System

The crystal system of the silicate glass sintered body was confirmed by measuring X-ray diffraction (XRD) patterns. For XRD diffraction analysis of the powdery silicate glass obtained by using the foregoing method, an XRD analyzer (RINT-TTR III, manufactured by Rigaku Corporation) using a CuKα radiation source was used for the measurement conducted with a measurement angle 2θ of 0° to 60°. In the silicate glass of the present invention, a crystalline phase is not necessarily required to be detectable in the XRD pattern.

Method of Measurement of Coefficient of Thermal Expansion

For the measurement of coefficient of thermal expansion, a sintered body prepared by firing the silicate glass was used as a specimen, and measured in compliance with ISO 6872:2015, specifically as follows.

The powdery silicate glass obtained by using the foregoing method was mixed with purified water to prepare a slurry. The slurry was charged into a cylindrical silicon frame measuring 7 mm in diameter×24 mm, and molded into a compact after repeated condensation and moisture absorption. At room temperature, the compact was placed in a furnace (a dental laboratory porcelain furnace Noritake KATANA™ F-1, manufactured by SK medical electronics Co., Ltd.), and was fired by being heated to the suitable firing temperature shown in Table 2. Immediately after firing, the compact was allowed to cool to room temperature to obtain a sintered body. The sintered body was then adjusted into a specimen measuring 5 mm in diameter×20 mm, using a grinder (hand grinder). The specimen was heated from a temperature of 24° C. or less to 550° C. at a rate of 5° C./min using a thermomechanical analyzer (Thermo plus TMA8310, manufactured by Rigaku Corporation), and the coefficient of thermal expansion was measured in the temperature range of 25 to 500° C. The evaluation results for Examples and Comparative Examples are presented in Table 2.

Method of Measurement of Color Difference (ΔEa*b*)

First, a commercially available zirconia disc (Noritake KATANA™ zirconia, disc HT-12, manufactured by Kuraray Noritake Dental Inc.) was cut into a plate shape (10 mm×10 mm×2 mm) to prepare a zirconia frame, using a diamond cutter.

This was followed by firing, in which the zirconia frame was heated from room temperature to 1,500° C. using a dental laboratory porcelain furnace (Noritake KATANA™ F-1, manufactured by SK medical electronics Co., Ltd.). After firing, the surface was ground to a thickness of 1.50 mm with a diamond grain abrasive paper under running water, and sandblasted with 0.05 mm alumina sand particles under 0.2 MPa to produce a matte surface. The resulting zirconia frame was then subjected to ultrasonic washing in acetone.

This was followed by fabrication of a specimen 1 having a porcelain layer formed on the zirconia frame to reproduce the enamel color of natural teeth. Specifically, the powdery silicate glass shown in Table 1 was used as a porcelain, and thoroughly mixed with solvent 2-phenoxyethanol in a porcelain mass-to-solvent mass ratio of 67:33. The porcelain-containing slurry was then applied to the zirconia frame surface, and heated to 1,500° C. for firing. The specimen 1 was obtained after grinding the porcelain layer to a thickness of 0.03 mm. Separately, a commercially available zirconia disc (KATANA™ zirconia, zirconia disc HT-12, manufactured by Kuraray Noritake Dental Inc.; coefficient of thermal expansion: $9.9 \times 10^{-6} K^{-1}$) was cut into a plate shape (10 mm×10 mm×2 mm) to prepare a zirconia frame, using a diamond cutter. This was followed by fabrication of a specimen 2 having a porcelain layer formed on the zirconia frame of unsintered body to reproduce the enamel color of natural teeth. Specifically, the silicate glass shown in Table 1 was used as a porcelain, and thoroughly mixed with solvent 2-phenoxyethanol in a porcelain mass-to-solvent mass ratio of 67:33. The porcelain-containing slurry was then applied to the frame surface, and heated to 1,500° C. for simultaneous firing of the zirconia frame and the porcelain. The specimen 2 was obtained after grinding the zirconia frame to a thickness of 1.50 mm, and the porcelain layer to a thickness of 0.03 mm.

The specimens 1 and 2 fabricated in the manner described above were measured for chromaticity (color space) in the L*a*b* color system in compliance with JIS Z 8781-4:2013, using a dental colorimeter (the Crystaleye Spectrophotometer CE100-DC, manufactured by Olympus Corporation). From the chromaticity (L*La*1,b*1) of specimen 1 and the chromaticity (L*2,a*2,b*2) of specimen 2, the color difference ΔEa*b* between (L*1,a*1,b*1) and (L*2,a*2,b*2) was calculated as follows.

$$\Delta Ea^*b^* = [(\Delta L^*)^2 + (\Delta a^*)^2 + (\Delta b^*)^2]^{1/2}$$

ΔEa*b* represents the difference due to the method of production, specifically, an index of color change (discoloration) of the zirconia base material. Larger values of ΔEa*b* mean greater discoloration, and smaller values of ΔEa*b* mean less discoloration. In view of ISO/TR 28642:2011, the preferred value of ΔEa*b* is 2.7 or less. ΔEa*b* is more preferably 2.0 or less, even more preferably 1.6 or less. The evaluation results for Examples and Comparative Examples are presented in Table 2.

TABLE 2

| | Suitable firing temperature (° C.) | Crystal system | Coefficient of thermal expansion (×10⁻⁶ K⁻¹) | Color difference ΔEa*b* |
|---|---|---|---|---|
| Example 1 | 1450 | Cristobalite | 5.4 | 0.94 |
| Example 2 | 1350 | Amorphous | 7.1 | 1.40 |
| Example 3 | 1200 | Amorphous | 6.1 | 1.58 |
| Example 4 | 1100 | Amorphous | 5.5 | 2.69 |
| Example 5 | 1450 | Cristobalite | 5.3 | 0.90 |
| Example 6 | 1100 | Amorphous | 5.6 | 2.67 |
| Com. Ex. 1 | 800 | Amorphous | 8.9 | 16.28 |
| Com. Ex. 2 | 1000 | Amorphous | 6.0 | 15.26 |

The silicate glass of Comparative Example 1 had a suitable firing temperature of 800° C., and was amorphous. As can be seen from above, the color difference in Comparative Example 1 was greater than any of the color differences observed in Examples 1 to 6. The silicate glass of Comparative Example 2 had a suitable firing temperature of 1,000° C., and was amorphous. The color difference in Comparative Example 2 was also greater than any of the color differences observed in Examples 1 to 6. In order to avoid defects and prevent discoloration in the base material, higher suitable firing temperatures are preferred for the silicate glass because the silicate glass is fired on the zirconia base material when simultaneously fired with the zirconia, for example. As can be seen in Table 2, the silicate glasses according to Examples 1 to 6 had higher suitable firing temperatures than the silicate glass according to Comparative Example 2, and the color difference between specimen 1 and specimen 2 was considerably smaller in Examples 1 to 6 than in Comparative Example 2. It can be seen from these results that the silicate glass of the present invention is suited as, for example, a dental porcelain simultaneously fired with zirconia.

While the silicate glass, the sintered body, the dental product, the method of use of the dental product, and the method of production of the dental product according to the present invention have been described through the embodiments above, the present invention is not limited to the foregoing embodiments, and may include various modifications, changes, and improvements to the elements disclosed (including the elements in the claims and in the embodiments and Examples) made within the full disclosure of the present invention on the basis of the basic technical idea of the present invention. Various combinations, replacements, and selections of the elements disclosed (including the elements in the claims and in the embodiments and Examples) are also possible within the boundaries of the full disclosure of the present invention.

INDUSTRIAL APPLICABILITY

A silicate glass of the present invention has a specific composition for its constituent components, and, because of the specific composition, has a high suitable firing temperature, enabling prevention of discoloration of the base material even when the base material and the ceramic are simultaneously fired. This makes the silicate glass of the present invention advantageous in terms of improving convenience and minimizing production time in manufacture of a dental product.

The invention claimed is:
1. A silicate glass comprising:
65.0 to 90.0 mol % $SiO_2$,
4.0 to 15.0 mol % $Al_2O_3$,
1.0 to 10.0 mol % $K_2O$,
0.1 to 7.0 mol % $Na_2O$, and
0.01 to 15.0 mol % CaO,
the silicate glass being essentially free of $B_2O_3$,
the content of $Li_2O$ being less than 0.1 mol %,
the content of an oxide of Tb being 0 mol %,
satisfying the relation {(number of moles of $Al_2O_3$)/(total number of moles of $RO+R_2O$)}≅0.70, wherein R in the metal oxide represented by RO represents a metallic element in group 2 or 12 of the periodic table, and R in the metal oxide represented by $R_2O$ represents a metallic element in group 1 of the periodic table.
2. The silicate glass according to claim 1, comprising:
69.0 to 89.0 mol % $SiO_2$,
5.0 to 13.0 mol % $Al_2O_3$,
3.0 to 9.0 mol % $K_2O$,
1.0 to 4.0 mol % $Na_2O$, and
0.05 to 13.0 mol % CaO,
the silicate glass being essentially free of $B_2O_3$, and satisfying the relation {(number of moles of $Al_2O_3$)/(total number of moles of $RO+R_2O$)}≥0.70.
3. The silicate glass according to claim 1,
wherein the silicate glass is essentially free of ZnO.
4. The silicate glass according to claim 1,
wherein the silicate glass is essentially free of MgO, BaO, and SrO.
5. The silicate glass according to claim 1,
wherein the silicate glass has a suitable firing temperature of 1,100° C. or more.
6. The silicate glass according to claim 1,
wherein the silicate glass has a coefficient of thermal expansion of 11.0×10⁻⁶ K⁻¹ or less as measured in compliance with ISO 6872:2015.
7. The silicate glass according to claim 1,
wherein the silicate glass further comprises at least one selected from the group consisting of a pigment and an opacifying agent.
8. A composite comprising the silicate glass of claim 1, and a ceramic.
9. The composite according to claim 8, wherein the ceramic is a zirconia ceramic.
10. A sintered body of the composite of claim 8.
11. A dental product comprising the sintered body of claim 10.

* * * * *